(12) United States Patent
Grover et al.

(10) Patent No.: US 7,091,174 B2
(45) Date of Patent: Aug. 15, 2006

(54) CALOXINS

(75) Inventors: Ashok K. Grover, Hamilton (CA); Emanuel Escher, Sherbrooke (CA); Jyoti Chaudhary, Cambridge (CA)

(73) Assignee: McMaster University, Hamilton (CA)

( * ) Notice: Subject to any disclaimer, the term of this patent is extended or adjusted under 35 U.S.C. 154(b) by 465 days.

(21) Appl. No.: 10/363,701

(22) PCT Filed: Oct. 5, 2001

(86) PCT No.: PCT/CA01/01409

§ 371 (c)(1),
(2), (4) Date: Oct. 10, 2003

(87) PCT Pub. No.: WO02/28886

PCT Pub. Date: Apr. 11, 2002

(65) Prior Publication Data

US 2004/0096898 A1    May 20, 2004

Related U.S. Application Data

(60) Provisional application No. 60/237,702, filed on Oct. 5, 2000.

(51) Int. Cl.
*A61K 38/00*    (2006.01)

(52) U.S. Cl. .......................................................... 514/2

(58) Field of Classification Search ..................... 514/2
See application file for complete search history.

(56) References Cited

OTHER PUBLICATIONS

Chaudhary, J. et al. "Caloxin: a novel plasma membrane Ca2+ pump inhibitor," American Journal of Physiology, 280(4 pt 1): C1027-C1030 (2001).
Kennedy B.G. and Mangini, N.J. "Plasma Membrane Calcium-ATPase in Cultured Human Retinal Pugment Epithelium," Experimental Eye Research, 63: 547-556 (1996).
Enyedi, A. and Penniston, J.T. "Autoinhibitory Domains of Various Ca2+ Trasnporters Cross-react," The Journal of Biological Chemistry, 268(23): 17120-17125 (1993).

*Primary Examiner*—Bruce R. Campell
*Assistant Examiner*—Maury Audet
(74) *Attorney, Agent, or Firm*—Micheline Gravelle; Bereskin & Parr

(57) ABSTRACT

Novel compound called caloxins which are extracellular plasma membrane (PM) $Ca^{2+}$-pump inhibitors are described. One caloxin is caloxin 2A1 and has the amino acid sequence VSNSNWPSFPSSGGG. Another caloxin is caloxin 3A1 and has the amino acid sequence DSHINNEPSRRRGGGK. The caloxins are useful in inhibiting PM $Ca^{2+}$-pumps and can be used in the development of treatments of various diseases including hypertension, hypotension, degenerative brain disorders, mood disorders, diabetes, kidney failure and cancer.

3 Claims, 3 Drawing Sheets

ND CALOXINS

FIELD OF THE INVENTION

The present invention relates to novel compounds called caloxins, methods for isolating caloxins and the use of caloxins in treating various diseases.

BACKGROUND OF THE INVENTION

Plasma membrane calcium pumps are $Ca^{2+}$—$Mg^{2+}$-ATPases that use the energy of hydrolysis of ATP to expel cellular $Ca^{2+}$. Plasma membrane (PM) $Ca^{2+}$ pumps are present in all mammalian cells. However, either PM Ca2+ pumps or Na+/$Ca^{2+}$ exchanger (8,9,17) may remove $Ca^{2+}$ from the cell after activation or during homeostasis, and the precise role of PM $Ca^{2+}$ pumps remains to be determined. There are no extracellular PM $Ca^{2+}$ pump inhibitors available to resolve this issue. In contrast, the $Na^+$ pump inhibitors ouabain and digoxin have been pivotal in our understanding of how this pump affects cell function (7, 12). The sarco(endo)plasmic reticulum $Ca^{2+}$-ATPase (SERCA) inhibitor thapsigargin, which can diffuse into the cell to act, has also proved very useful in elucidating the role of the SERCA pump (15). PM $Ca^{2+}$ pumps are encoded by four plasma membrane $Ca^{2+}$-ATPase (PMCA) genes, and their transcripts can be alternatively spliced (2, 4, 10, 14). The isoform PMCA1b is most widely expressed. The PM $Ca^{2+}$ pump protein models show ten transmembrane and five extracellular domains (4). Except for the first putative extracellular domain, their sequences are conserved in different isoforms. All the known functions of the pump are assigned to the cytosolic domains, although mutagenesis of key residues in the PM $Ca^{2+}$ pump protein shows that transmembrane domains are involved in its activity (5). X-ray diffraction studies of the sarcoplasmic reticulum $Ca^{2+}$ pump also support a role for transmembrane domains in the pump activity (16). In contrast, it is unknown whether extracellular domains in the PM $Ca^{2+}$ pump play any role in its function.

There is a need in the art to provide inhibitors of the plasma membrane $Ca^{2+}$ pump.

SUMMARY OF THE INVENTION

The present invention relates to novel compounds called caloxins which are extracellular plasma membrane (PM) $Ca^{2+}$-pump inhibitors. Accordingly, one aspect of the present invention relates to an isolated caloxin that can inhibit a plasma membrane $Ca^{2+}$-pump.

In one embodiment, the caloxin is a peptide having the sequence VSNSNWPSFPSSGGG (SEQ.ID.NO.1). This caloxin is generally termed caloxin 2A1. In another embodiment the caloxin is a peptide having the sequence DSHINNEPSRRRGGGK (SEQ.ID.NO.2). This caloxin is generally termed caloxin 3A1.

The invention also extends to fragments, analogs and derivatives of these peptides which maintain the ability to inhibit a plasma membrane $CA^{2+}$-pump.

The present invention also relates to methods for isolating caloxins comprising screening a random peptide phage display library with a peptide fragment from a PMCA protein and isolating peptides that bind to the PMCA peptide fragment. Peptides that bind to the PMCA peptide fragment can be tested for caloxin activity, for example by testing its ability to inhibit erythrocyte leaky ghost $Ca^{2+}$—$Mg^{2+}$-ATPase.

The present invention includes the use of the caloxins of the present invention in research, in the treatment of various diseases and in the preparation of modulators of caloxins or a PM $Ca^{2+}$-pump such as antibodies, antisense molecules or peptide mimetics.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

The following standard one letter and three letter abbreviations for the amino acid residues may be used throughout the specification: A, Ala—alanine; R, Arg—Arginine; N, Asn—Asparagine; D, Asp—Aspartic acid; C, Cys—Cysteine; Q, Gln—Glutamine; E, Glu—Glutamic acid; G, Gly—Glycine; H, His—Histidine; I, Ile—Isoleucine; L, Leu—Leucine; K, Lys—Lysine; M, Met—Methionine; F, Phe—Phenylalanine; P, Pro—Proline; S, Ser—Serine; T, Thr—Threonine; W, Trp—Tryptophan; Y, Tyr—Tyrosine; and V, Val—Valine.

As hereinbefore mentioned, the present invention relates to novel compounds called caloxins, methods of isolating the caloxins as well as all uses of the caloxins.

I. Caloxins

The term "caloxin" as used herein means an extracellular plasma membrane (PM) $Ca^{2+}$-pump inhibitor. Accordingly, the present invention provides an isolated caloxin which can inhibit a plasma membrane $Ca^{2+}$-pump. In a preferred embodiment, the caloxin is caloxin 2A1 which comprises the sequence VSNSNWPSFPSSGGG (SEQ.ID.NO.1), caloxin 3A1 which comprises the sequence DSHINNEPSR-RRGGGK (SEQ.ID.NO.2), or a caloxin which comprises the sequence VSNSNWPSFPSS (SEQ.ID.NO.6) as well as fragments, elongations, analogs and derivatives of the caloxins which maintain the ability to inhibit a plasma membrane $Ca^{2+}$-pump.

The term "analog" includes any peptide having an amino acid residue sequence substantially identical to the sequence of a caloxin described herein in which one or more residues have been conservatively substituted with a functionally similar residue and which displays the ability to mimic a caloxin. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glutamine and glutamic acid, between asparagine and aspartic acid, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term "derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino add derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

Caloxins of the present invention also include any peptide having one or more additions and/or deletions or residues relative to the sequence of a caloxin whose sequence is shown herein, so long as the requisite activity is maintained or increased.

The term "fragment" refers to any subject peptide having an amino acid sequence shorter than that of a caloxin whose amino acid sequence is shown herein.

The term "elongation" refers to any subject peptide having an amino acid sequence longer than that of a caloxin whose amino acid sequence is shown herein.

The invention also includes isolated nucleic acid sequences encoding a caloxin. In one embodiment, an isolated nucleic acid molecule is provided having a sequence which encodes caloxin 2A1 comprising the amino acid sequence shown in SEQ.ID.NO.1. In another embodiment, an isolated nucleic acid molecule is provided having a sequence which encodes caloxin 3A1 comprising the amino acid sequence shown in SEQ.ID.NO.2. In a further embodiment an isolated nucleic acid molecule is provided having a sequence which encodes a caloxin having the amino acid sequence shown in SEQ.ID.NO.6.

It will be appreciated that the invention includes nucleic add molecules encoding truncations of proteins of the invention, and analogs and homologs of proteins of the invention and truncations thereof, as described above. It will further be appreciated that variant forms of nucleic add molecules of the invention which arise by alternative splicing of an mRNA corresponding to a cDNA of the invention are encompassed by the invention.

Isolated and purified nucleic add molecules having sequences which differ from the nucleic add sequence of the invention due to degeneracy in the genetic code are also within the scope of the invention. Such nucleic acids encode functionally equivalent proteins but differ in sequence from the above mentioned sequences due to degeneracy in the genetic code.

II. Methods of Isolating Caloxins

The present invention also includes a method of isolating caloxins comprising screening a random peptide phage display library with a peptide fragment from a PMCA protein and isolating peptides that bind to the PMCA peptide fragment.

The peptide fragment from the PMCA protein is preferably from an extracellular domain of the PMCA protein. In particular, the inventors have designed the peptide PMCA398 (WVQKRPWLAESTPIYIQYFVKC, SEQ.ID.NO.3) based on residues 398–418 of PMCA1 (Genbank X59069) and conjugated it through the terminus cysteine to keyhole limpet hemocyanin or ovalbumin. The inventors screened an MEK13 random peptide phage display library (New England Biolabs, USA) and identified a phage that bound to the PMCA398-keyhole limpet hemocyanin conjugate and eluted with the PMCA398-ovalbumin. Specific details on the screening assay are provided in Example 1. A peptide containing the 12 amino add recognition sequence and a spacer (VSNSNWPSF-PSSGGG-amide, SEQ.ID.NO.1) was synthesized and subsequently termed caloxin 2A1.

The inventors further designed the peptide PMCA 874 (KITQGSPLKA, SEQ.ID.NO.4) based on residues 874–994 of PMCA1. This PMCA peptide was used to screen a random phage display library as described above which resulted in the isolation of the peptide caloxin 3A1 which has the sequence Acetyl-DSHINNEPSRRRGGGK (SEQ.ID.NO.2).

Figure 1:
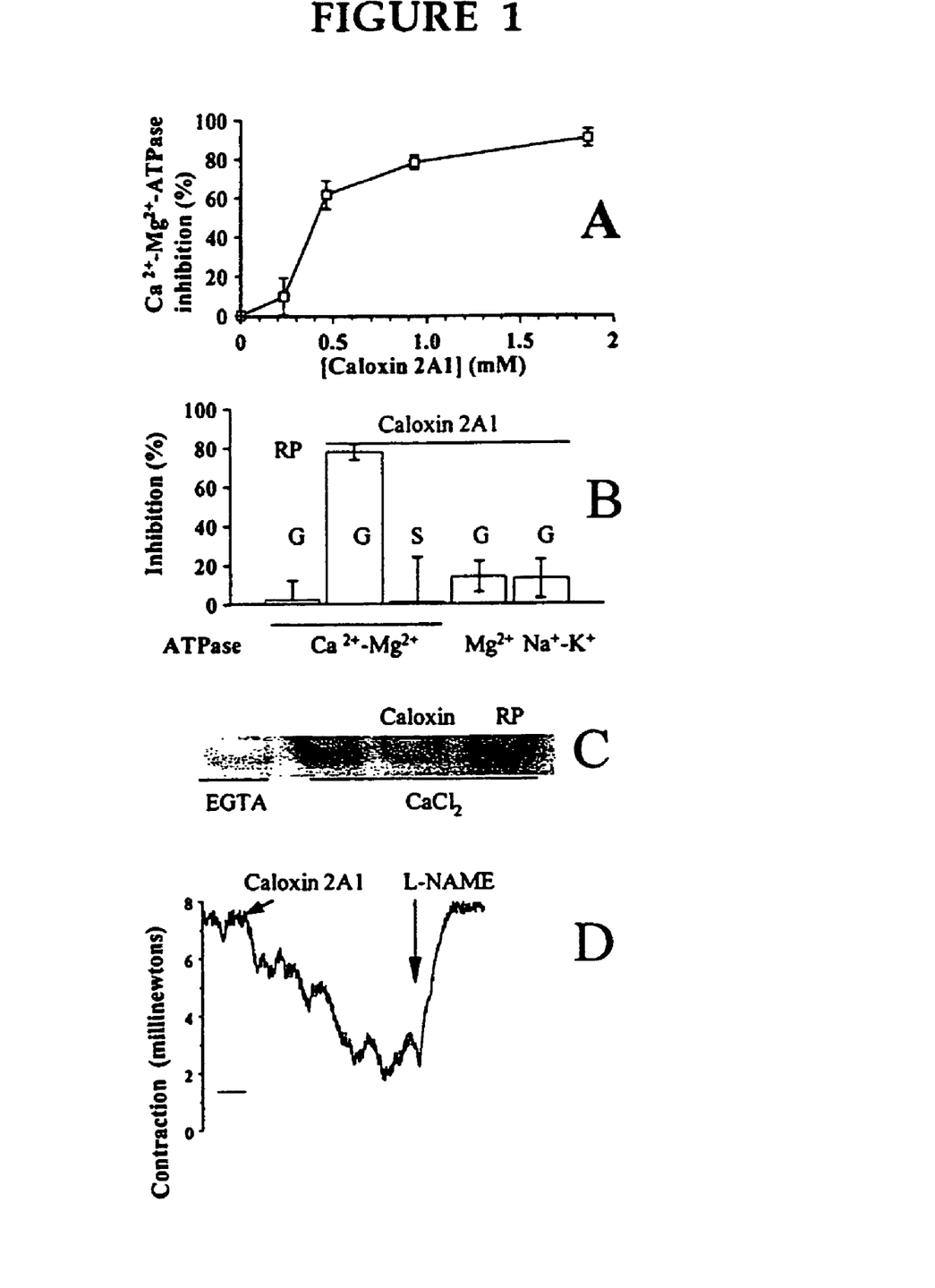
FIG. 1A is a graph showing $Ca^{2+}$—$Mg^{2+}$-ATPhase inhibition by caloxin 2A1. Human erythrocyte leaky ghosts (Jarrett et al. (1978)) were assayed for ATPase as described previously (Niggli et al. (1981); Grover (1988)) but by fluorometry. The drawn curve is from a total of 32 data points. Error bars where shown are SEM values.
FIG. 1B is a bar graph showing the selectivity of caloxin 2A1 for inhibition of PM $Ca^{2+}$—$Mg^{2+}$-ATPase using caloxin 2A1 or a random peptide (RP). G=ghosts and S=skeletal muscle sarcoplasmic reticulum, Type of ATPhase activity monitored is shown as $Ca^{2+}$—$Mg^{2+}$, $Mg^{2+}$ or $Na^+$—$K^+$-ATPase. The only significant (p<0.05) inhibition was by caloxin 2A1 in the ghosts.
FIG. 1C is gel showing acylphosphate formation with 3.4 mM caloxin 2A1 or a random peptide. The acylphosphate reaction was carried out and samples analyzed by acid gel electrophoresis as previously described (Grover et al. (1988); Wuytack et al. (1984)). EGTA=1 mM, and $CaCl_2$=0.05 mM.
FIG. 1D is a graph showing endothelium dependent relaxation of rat aorta. Rat aorta rings were hung in organ bath as previously described. The rings were contracted with submaximum (0.5 µM) phenylephrine before adding 0.34 mM caloxin 2A1 and 0.1 mM L-nitroarginylmethyl ester) as shown. Each experiment was replicated at least four times.

The present invention includes all caloxins isolated according to the method of the invention. Caloxins can be tested for their ability to inhibit the plasma membrane $Ca^{2+}$-pump using various assays. In particular, PM $Ca^{2+}$ pump is a $Ca^{2+}$—$Mg^{2+}$-ATPase that binds ATP in presence of $Ca^{2+}$ to form an acylphosphate which is then hydrolysed upon $Ca^{2+}$ translocation (Guerini (1998)). The effect of caloxins on PM $Ca^{2+}$ pump can be tested in two assays using human erythrocyte leaky ghosts: $Ca^{2+}$—$Mg^{2+}$-ATPase and acylphosphate formation. In particular the inventors have shown that caloxin 2A-1 inhibits erythrocyte leaky ghost Ca$^{2+}$—Mg$^{2+}$-ATPase (FIG. 1A) producing 50% inhibition at 0.4±0.1 mM. Caloxin 2A-1 inhibits the PM Ca$^{2+}$-pump selectively. At a concentration of 0.9 mM, caloxin 2A1 inhibits the erythrocyte ghost Ca$^{2+}$—Mg$^{2+}$-ATPase by 78±4% but with no effect on Mg$^{2+}$-ATPase or Na$^{+}$—K$^{+}$-ATPase in the ghosts or the Ca$^{2+}$—Mg$^{2+}$-ATPase in skeletal muscle sarcoplasmic reticulum (FIG. 1B). The inhibition is selective to caloxin 2A1 because 0.9 mM of a peptide with randomized caloxin 2A1 sequence (SWSSFPGSGGVS-NPN-amide, SEQ.ID.NO.5) has no effect (FIG. 1B) neither does the large mixture of peptides contained in the casein pancreatic hydrolysate (data not shown). Thus, caloxin 2A1 is selective in that it inhibits the PM Ca$^{2+}$-pump and not other ATPases. However, it does not appear to distinguish between different isoforms of the PM Ca$^{2+}$-pump. Caloxin 2A1 was selected by binding to a PMCA1 sequence but it inhibits PM Ca$^{2+}$-pump in erythrocyte ghosts which express mainly PMCA4. This finding is consistent with the high degree of similarity between sequences of PMCA genes in this domain (Swiss Protein Bank accession numbers P20020, Q01814, Q16720, P23634) although we have not ruled out that caloxin 2A1 has different affinities for each isoform. The second PM Ca$^{2+}$-pump assay consisted of Ca$^{2+}$-dependent formation of the acid stable 140 kDa acylphosphate intermediate from $^{32}$P-γ-ATP in erythrocyte leaky ghosts. Caloxin 2A1 inhibits the acylphosphate formation but the randomized peptide does not (FIG. 1C).

Inhibiting the PM Ca$^{2+}$ pump in vascular endothelium should increase cytosolic Ca$^{2+}$, thereby activating endothelial nitric oxide synthase to relax arteries (Rees et al. (1990); Sato et al. (1990)). In rat aortic rings precontracted with phenylephrine, caloxin 2A1 produced a relaxation which was reversed by the nitric oxide synthase inhibitor L-nitroarginylmethyl ester (L-NAME) (FIG. 1D). Thus caloxin 2A1 produced the biological effect in the endothelium which was expected from its inhibiting PM Ca$^{2+}$-pump.

III. Uses of the Caloxins

The present invention also includes all of the uses of the caloxins of the present invention. As both the Na$^{+}$-pump and the PM Ca$^{2+}$-pump are central to the function of every cell, caloxins have important and wide ranging utilities. The isolation of the caloxins of the invention also enables the preparation of other modulators of caloxin and/or the PM Ca$^{2+}$-pump. Such modulators include antibodies, antisense molecules and peptide mimetics.

(a) Antibodies

The caloxins of the invention may be used to prepare antibodies to the caloxins. Conventional methods can be used to prepare the antibodies including polyclonal antisera or monoclonal antibodies. To produce polyclonal antibodies, a mammal, (e.g., a mouse, hamster, or rabbit) can be immunized with an immunogenic form of the caloxin which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al., Monoclonal Antibodies in Cancer Therapy (1985) Allen R. Bliss, Inc., pages 77–96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein, of the invention, or peptide thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a protein of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a caloxin of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great. Britain).

Specific antibodies, or antibody fragments, reactive against a caloxin of the invention may also be generated by screening expression libraries encoding immunoglobulin genes, or portions thereof, expressed in bacteria with the ligands of the invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)).

(b) Antisense Oligonucleotides

The nucleic acid molecules encoding the caloxins of the invention can also be used to prepare antisense oligonucleotides against the caloxins. Accordingly, the present invention provides an antisense oligonucleotide that is complementary to a nucleic acid sequence encoding a caloxin.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics. The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo.

(c) Peptide Mimetics

The present invention also includes peptide mimetics of the caloxins of the invention. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243–252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides of the invention may also be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds that can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess.

(d) Therapeutic Uses

The caloxins and modulators thereof can be used to inhibit a plasma membrane (PM) $Ca^{2+}$-pump. Accordingly, in one embodiment, the present invention provides a method of inhibiting a PM $Ca^{2+}$-pump comprising administering an effective amount of a caloxin or a modulator thereof to a cell or animal in need thereof. The invention also includes a use of a caloxin or a modulator thereof in order to prepare a medicament to inhibit a PM $Ca^{2+}$-pump.

The term "modulator" includes agents that inhibit or enhance the activity of a caloxin of the invention and includes antibodies, antisense molecules and peptide mimetics. Such caloxin modulators may also modulate a PM $Ca^{2+}$-pump.

The term "effective amount" as used herein means an amount effective, at dosages and for periods of time necessary to achieve the desired result.

The term "animal" as used herein includes all members of the animal kingdom, including humans. Preferably, the animal to be treated is a human.

The caloxins of the invention can also be used as reagents to understand the function of PMCA ATPase in physiology and pathophysiology. Since different forms of PMCA ATPase are present in various cells in the body, this reagent would have broad uses to study cell function in heart, smooth muscle and endothelium of arteries and veins, cells in kidney, pancreas and brain.

In addition, as mentioned above, the caloxins of the invention can be used to construct modulators (including inhibitors and activators) of PMCA ATPase with greater tissue selectivity either based on differences in structures of the pumps or bioavailability of the drugs by designing peptide and nonpeptide substances. It is expected that caloxins will cause an endothelium-dependent relaxation and hence it will be a useful drug for hypertension or atherosclerosis where it may also be useful to relax partially blocked arteries. As an inhibitor of vascular smooth muscle it may be useful in hypotension. Different tissues have different forms of this enzyme. Therefore, this discovery may also be used for degenerative brain diseases, mood disorders, diabetes, kidney failure and cancer.

Accordingly, the present invention provides a method of treating a disease wherein it is desirable to inhibit a PM $Ca^{2+}$-pump comprising administering an effective amount of a caloxin or a modulator thereof to an animal in need thereof. The present invention also provides a use of a caloxin or a modulator thereof to prepare a medicament to treat a disease wherein it is desirable to inhibit a PM $Ca^{2+}$-pump. Such diseases may be selected from the group consisting of hypertension, hypotension, degenerative brain diseases, mood disorders, diabetes, kidney failure and cancer.

(e) Compositions

The present invention also includes pharmaceutical compositions comprising caloxins of the invention or a modulator thereof. Accordingly, the present invention provides a pharmaceutical composition comprising an effective amount of a caloxin or a caloxin modulator and a pharmaceutically acceptable diluent or carrier.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

In accordance with the methods of the invention, the described compositions may be administered to a patient in a variety of forms depending on the selected route of administration, as will be understood by those skilled in the art. The compositions of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A composition of the invention or a salt or solvate thereof may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A composition of the invention may also be administered parenterally or intraperitoneally. Under ordinary conditions of storage and use, these composition contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

The compositions of the invention may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of the invention may be administered initially in a suitable dosage that may be adjusted as required, depending on the clinical response.

The following non-limiting examples are illustrative of the present invention:

EXAMPLES

Example 1

Isolation of Caloxins 1.1. Leaky Ghost Preparation (Modified from Jarret & Penniston 1978 JBC 253.4676)

All preparation is to be carried out at 0–4° C. with buffers precooled to that temperature.

1. Human blood in acid citrate dextrose. Centrifuge once at 4000 g for 5 min to remove the plasma and buffy coat (containing platelets) and keep the lower layer.

2. Add 10 volumes of 172 mM Tris-HCl pH 7.6 at 4° C. Mix and centrifuge at 8000 rpm for 5 min in a J14 rotor. Remove dear supernatant by suction.

3. Repeat step 2 four times.

4. Pool the cells from all tubes to a minimum number of tubes. Use the minimum amount of buffer needed to make the transfer complete. Centrifuge at 8000 rpm for 5 min in a J14 rotor. Remove clear supernatant.

5. Dilute into 14 volumes of chilled water. Mix and put into 250 ml centrifuged bottles.

6. Centrifuge at 12000 rpm for 10 min in a J14 rotor. Remove the red liquid by suction leaving 30 ml/tube at the bottom.

7. To each tube add 150 ml imidazole-EDTA (10 mM imidazole-HCl, 1 mM EDTA pH 7.0 at 23° C.).

8. Centrifuge at 12000 rpm for 10 min in a J14 rotor.Remove the red liquid by suction leaving behind 30 ml (loose pellet and tight pellet).

9. Add imidazole-EDTA to fill the bottles to two third level. Centrifuge at 12000 rpm for 10 min in a J14 rotor. Remove the red liquid by suction leaving behind 30 ml (loose pellet and tight pellet).

10. Add imidazole-EDTA to fill the bottles to the two third level. Centrifuge at 12000 rpm for 10 min in a J14 rotor. Remove the red liquid by suction leaving behind 30 ml (loose pellet and tight pellet). Repeat until the supernatant is colourless.

11. Finally transfer the loose pellet into new 250 ml tubes and add to it 14 volumes imidazole-HCl buffer (pH 7 at 23° C., no EDTA). Centrifuge at 12000 rpm for 10 min.

12. Repeat the step 11. Finally concentrate the white loose pellets into minimum number of 50 ml centrifuge tubes and centrifuge at 18000 rpm for 10 min.

13. Aliquot the pellet into three 50 ul Eppendorf tubes for protein estimation and remaining into 1 ml Eppendorf tubes for the $Ca^{2+}$—$Mg^{2+}$-ATPase assay and freeze at −80° C.

1.2. $Ca^{2+}$—$Mg^{2+}$-ATPase assay with human erythrocyte leaky ghosts: A major hurdle was the lack of an appropriate assay. The difficulties were: (a) calmodulin needed for the PM $Ca^{2+}$ pump activity binds on the cytosolic surface of the pump protein and caloxins by definition bind on the outside surface, (b) most tissues have very active ecto-$Mg^{2+}$-ATPase and an ER $Ca^{2+}$—$Mg^{2+}$-ATPase—the latter can be inhibited by thapsigargin but the former poses a major problem. Erythrocyte ghosts contain mostly plasma membrane. Finally we used human erythrocyte ghosts which have low ecto-$Mg^{2+}$-ATPase. Fluorometric coupled enzyme assays are more sensitive. We purchased microcuvettes (100–150 µl) for our fluorometer (SPEX Fluorolog 112) with a heated chamber (37° C.) and made the appropriate cuvette adapter. We first monitor basal $Mg^{2+}$-ATPhase as slope for the disappearance of NADH fluorescence (ex=340, em=440 nm) in a solution containing 0.2–0.4 mg ghost protein, 0.1 mM ouabain, 100 mM NaCl, 20 mM KCl, 6 mM $MgCl_2$, 30 mM imidazole-HCl pH 7.0, 0.5 mM EDTA, 0.6 mM NADH, 1 mM pyruvate enol phosphate, excess pyruvate kinase-acetate dehydrogenase, 0.5 mM ATP, 0.5 mM EGTA and 4 ug/ml calmodulin. Then we add 0.55 mM $CaCl_2$ and determine the slope again. Difference between the two slopes is the $Ca^{2+}$—$Mg^{2+}$-ATPase. $Na^+$—$K^+$-ATPase can be monitored without $CaCl_2$ and ouabain.

Figure 3:
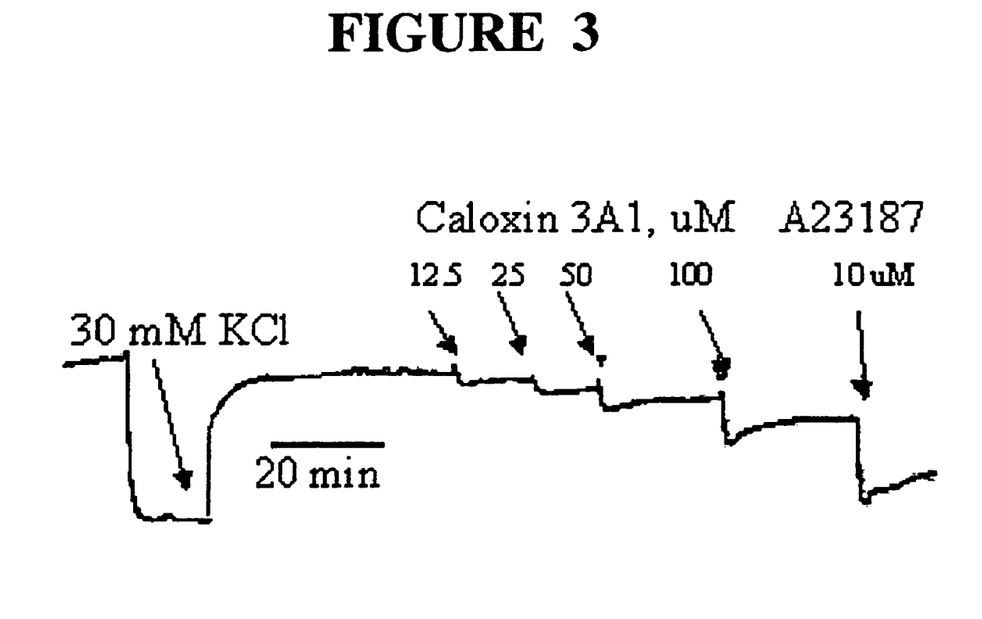
FIG. 3 illustrates endothelium dependent relaxation by caloxin 3A1 in pig coronary artery pre-contracted with KC1.

1.3. Contractility experiments: We chose to use rat aorta in these experiments due to its endothelium dependent relaxation to acetylcholine or carbachol. We anesthetized a rats by methoxyfluorane (Metofane) inhalation and removed its thoracic aorta as 3 mm rings. These tissues relax to 1 µM carbachol after they have been contracted with phenylephrine (0.5 to 2 µM). We initially tried to do these experiments in $Na^+$-free solution but the tissues gave very poor contractions to phenylephrine. In $Na^+$-free solution, the tissues contracted to 20–80 mM KCl but relaxation with carbachol was poor. We reverted to using phenylephrine but in $Na^+$-containing Krebs' solution. Caloxin 2A1 relaxed the aortic rings (App. B1). Caloxin 3A1 produces an endothelium dependent relaxation in coronary arteries precontracted with KCl (FIG. 3). FIG. 3 shows the relaxation of KCl contracted pig coronary arteries with caloxin 3A1.

Figure 2:
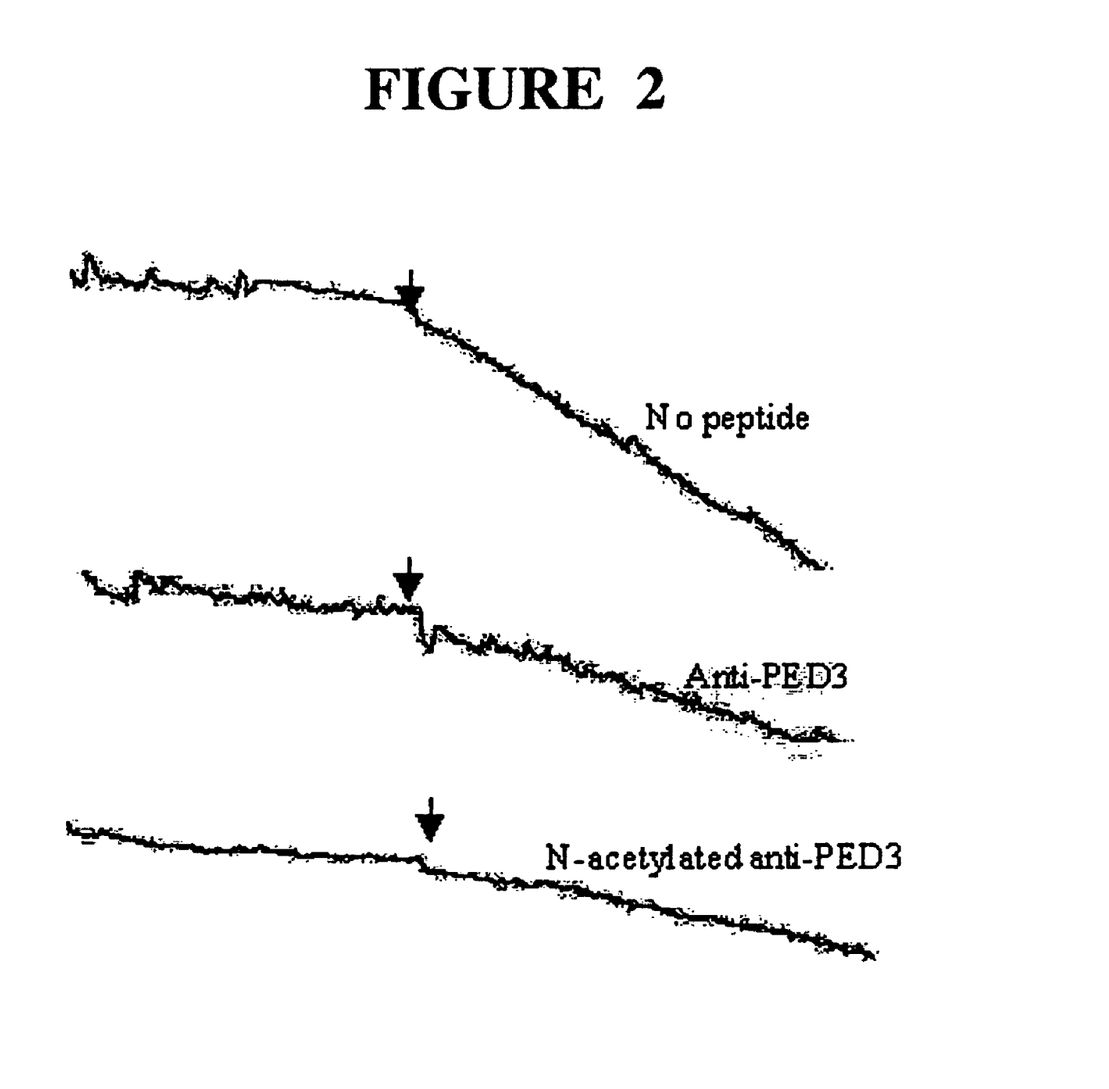
FIG. 2 illustrates that an anti-PED3 inhibits $Ca^{2+}$—$Mg^{2+}$-ATPase in erythrocyte leaky ghosts. All traces span 20 min. Y-axis is the same relative fluorescence scale for each tracing. Reaction was started in a solution containing EGTA and $CaCl_2$ added where shown by arrow.

1.4. Screening phage display library for anti-PED2 and anti-PED3: We chose targets which are potentially on the outside surface of PMCA1b: 401–413 and, 880–884 (see FIG. 2). Based on these sequences, we synthesized the peptides PMCA398:WVQKRPWLAESTPIYIQYFVKC (SEQ.ID.NO.3), and PMCA874: KITQDSPLKA (SEQ.ID.NO.4).

The N-terminal residue was added for conjugating the peptides to keyhole-limpet hemocyanin (KHLH) and ovalbumin.

1.4.1. Screening strategies: PhD12 (New England Biolabs) is a phage display library which expresses random 12-mer peptides in the vector M13KE (see App. B3). The overall strategy was to bind the target peptide to a microtiter plate well, wash off the excess peptide, block the remaining binding sites in the well, remove excess blocking solution, place the phage in the well and incubate, wash off unbound phage, optimize the wash conditions using different solutions and wash times, and then elute the phage at low pH or with the target peptide. The objective was to obtain a phage done that binds selectively to PMCA398 or PMCA874. We tried several different conditions for the wash and elution. Initially we worked with 3 different host strains as the host in the kit did not work reproducibly.

1.4.2. Selectivity Assay: We monitored success of the screening procedures using a selectivity assay. If a phage was selective for binding to PMCA398, more phage would be eluted when with KHLH-398 is used in the wells for binding and ovalbumin-398 is used for the elution than with binding is to KHLH and elution is with ovalbumin. Following is a summary of the individual steps in the assays.

1. Coat U-welled microtitre plates with 150 µl of 0.1 mg/ml KHLH-398 (well one) or KHLH (well two) in coating buffer (0.1 M NaHCO$_3$, 0.5% bovine serum albumin, 1 mM Na-azide pH with HCl to 7.4). Incubate overnight at 4° C.

2. Empty well. Incubate for 60 min with blocking solution (5% BSA and 1 mM azide) in PBS (137 mM NaCl, 2.7 mM KCl, 8 mM Na$_2$HPO$_4$ and 1.5 mM KH$_2$PO$_4$, pH 7.4) at 4° C.

3. Wash 6× with PBS.

4. Incubate while rocking at 20–23° C. for 60 min with 100 µl phage ($10^9$–$10^{11}$ pfu) diluted in blocking solution.

5. Wash 10× with PBS (no azide).

6. Incubate while rocking for 5 min at 20–23° C. with KHLH-Blotto (PBS containing 10% carnation skim milk and 1 mg/ml KHLH but no azide).

7. Wash 1× with PBS (no azide).

8. Elute phage while rocking for 20 min at 20–23° C. with 100 µl of PBS containing 0.5 mg/ml of ovalbumin-398 (no azide) for the first well and ovalbumin for the second.

9. Titer the eluted phage using XL-1 blue cells. For titer, culture cells in LB-tetracyclin from single colony on the day of the titer to a density of 0.3–0.6. Centrifuge cells and resuspend in LB without tetracyclin (25% volume of the original).

Note: Azide is included in the initial steps to avoid bacterial/fungal growth. However, azide is exduded from steps 6 to 11 to ensure that it does not interfere with the growth of XL-1 blue cells.

1.4.3. Screening Procedure for PMCA874: Below is single cycle of the final panning procedure used to screen against the target peptide PMCA874.

1. Coat U-welled microtiter plates with 150 µl of 0.1 mg/ml KHLH-874 in coating buffer (0.1 M NaHCO$_3$, 0.5% bovine serum albumin, 1 mM Na-azide pH with HCl to 7.4). Incubate overnight at 4° C.

Steps 2 to 7 were as for the selectivity assay.

8. Elute phage while rocking for 30 min at 20–23° C. with 100 µl of PBS containing 0.5 mg/ml of ovalbumin-874 (no azide).

9. Mix 80 µl of the eluted phage, 200 µl XL-1 cells (OD 0.3–0.6) and 800 µl LB. Shake for 4–5 h at 37° C. The XL-1 blue cells were cultured from stock on an LB-agar tetracyclin plate, a single colony was used to obtain overnight cultures in tetracyclin and then 1 ml of cells were cultured in 100 ml LB-tetracyclin.

10. Centrifuge the cultures. To the medium add 200 µl of a solution containing 20% polyethylene glycol and 2.5 M NaCl. Let sit overnight. Centrifuge 15 min to obtain the phage pellet. Suspend the phage pellet in 100 µl PBS to obtain stock phage for further use.

We panned for 6 cycles using this protocol and then assayed it for selectivity. Using KHLH-874 to attach the phage and ovalbumin-874 to elute it gave 154000 pfu/µl while that using KHLH to attach and ovalbumin to elute gave 60000 pfu/µl giving a selectivity ratio of 154000/60000=2.5 compared to the library which gives a value of 1 for this parameter.

We panned for two more rounds and picked clones after round 8. We then tested each clone using the selectivity assay. Two of the clones consistently gave positive results: 8:11 and 8:12. We purified clones 11 and 12. We sequenced single stranded DNA from 12 subclones derived from these using the −28 and −96 primers provided in the PhD12 kit. The consensus sequence encoded a unique peptide which in a preliminary experiment inhibits erythrocyte ghost Ca$^{2+}$—Mg$^{2+}$-ATPase (FIG. 2) and we have now termed it caloxin 3A1.

1.4.4. Screening Procedure for PMCA398: The peptide PMCA398 is extremely hydrophobic. Therefore, it was conjugated at a lower (5:1 molar) ratio to KHLH and ovalbumin. The peptide and its conjugates could be used only at low concentrations as very fine suspensions. The strategy used for PMCA874 did not yield positive results in selectivity assays. Therefore, a strategy of sequentially increasing selectivity was used. First three rounds of panning were conducted at low stringency. Wells were coated with either KHLH-398 or free 398 dissolved in PBS or coating buffer. After the phage binding, the plates were washed for 2 min in 5 mg/ml BSA, 0.5 mg/ml ovalbumin and 0.5 mg/ml KHLH and then 10× in PBS before elution with ovalbumin-398. The selected phage were pooled. The plates were coated with a mixture of KHLH398 and 398 and selected three times at higher stringency by using the above wash followed by 4 washes with 50 mg/ml carnation milk and 4 additional washes with PBS but all the washes were carried out at 0° C. After three high stringency washes, a differential time elution was performed—at each time point replacing the elutant with new PBS. The idea was that the most tightly bound phage would elute last. The elution was at room temperature for 1, 2, 4, 8, 16 and then 120 min. The phage from 16 and 120 min elutants gave excellent results in selectivity assays. DNA from 20 clones was sequenced and 8 clones gave a consensus sequence encoding the 12 amino acid peptide VSNSNWPSFPSS (SEQ.ID.NO.6). VSNSNWPSFPSSGGG-amide (SEQ.ID.NO.1) was synthesized as anti-PMCA398. Genbank search showed anti-PMCA398 to have 63% identity with 11 residues of alpha-2 adrenergic receptor (SWPAFPNSGEG, SEQ.ID.NO.7) and 54% with 11 residues of catalase (NQGNWPNYPSS, SEQ.ID.NO.8).

Example 2

Testing Caloxin 2A1 with Different Isoforms of PM Ca$^{2+}$-Pumps

PM Ca$^{2+}$-pump isoforms are encoded by 4 different genes. The inventors determined the effects of caloxin 2A1 on different isoforms. Cos M6 cells were transfected with this DNA using Fugene (purchased from Roche). Microsomes from SF9 cells expressing PMCA2 were a gift from Dr. A. Filoteo.

PMCA4 plasmid was transfected into COS-M6 cells. Thirty six to 48 hr later, microsomes were made from these cells and overexpression of the protein was confirmed using Western Blot. The Ca$^{2+}$—Mg$^{2+}$-ATPase activity in the microsomes was determined. The assay solutions included the following additional reagents: 0.05% Triton X-100, 5 mM sodium azide and 10 uM cyclopiazonic acid. Results: In a total of 22 determinations, the inhibition produced by 0.46, 0.94 and 1.87 mM caloxin 2A1 on PMCA4 was 29, 47 and 58%, respectively. In another two experiments PMCA2b was inhibited with 1.87 mM by an average inhibition of 46%.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended All publications, patents and patent applications are herein incorporated by reference in their entirety to the same extent as if each individual publication, patent or patent application was specifically and individually indicated to be incorporated by reference in its entirety.

Full Citations for References Referred to in the Specification

1. Grover A I L Monoclonal antibody against an epitope on the cytoplasmic aspect of the plasma membrane calcium pump. J Biol Chem 263: 19510–19512, 1988.
2. Grover A K and Ehan 1. Calcium pump isoforms: diversity, selectivity and plasticity. Cell Calcium 13:9–17, 1992.
3. Grover A K and Samson S E. Effect of superoxide radical on $Ca^{2+}$ pumps of coronary artery. Am J Physiol Cell Physiol 255: C297–C303, 1988.
4. Guerini D. The significance of the isoforms of plasma membrane calcium ATPase. Cell Tissue Res 292: 191–197, 1998.
5. Guerini D, Foletti D, Vellani F, and Carafoli E. Mutation of conserved residues in transmembrane domains 4, 6, and 8 causes loss of Ca" transport by the plasma membrane Ca21 pump. Biochemistry 35: 3290–3296, 1996.
6. Jarrett H W and Penniston J T. Purification of the $Ca^{2+}$-stimulated ATPase activator from human erythrocytes. Its membership in the class of $Ca^{2+}$-binding modulator proteins. J Biol Chem 253:4676–4682,1978.
7. McDonough A A, Wang J, and Farley R A. Significance of sodium pump isoforms in digitalis therapy. J Mol Cell Cardiol 27:1001–1009,1995.
8. McNaughton P A. Fundamental properties of the Na—Ca exchange. An overview. Ann AT Acad Sci 639:2–9, 1991.
9. Niggli V, Adunyah E S, Penniston J T, and Carafoli E. Purified ($Ca^{2+}$,—$Mg^{2+}$)-ATPase of the erythrocyte membrane. Reconstitution and effect of calmodulin and phospholipids. J Biol Chem 256:395–401,1981.
10. Raeymaekers L and Wuytack F. $Ca^{2+}$ pumps in smooth muscle cells. J Muscle Res Cell Motil 14: 141–157, 1993.
11. Rees D D, Palmer R M, Schulz R, Hodson H F, and Moncada S. Characterization of three inhibitors of endothelial nitric oxide synthase in vitro and in vivo. Br J Pharmacol 101: 746–752, 1990.
12. Rose A M and Valdes R J. Understanding the sodium pump and its relevance to disease. Clin Chem 40: 1674–1685, 1994.
13. Sato K, Ozaki H, and Karaki H. Differential effects of carbachol on cytosolic calcium levels in vascular endothelium and smooth muscle. J Pharmacol Exp Ther 255: 114–119, 1990.
14. Stauffer T P, Guerini D, and Carafoli E. Tissue distribution of the four gene products of the plasma membrane Ca 21 pump. A study using specific antibodies. J Biol Chem 270: 12184–12190, 1995.
15. Thastrup O, Dawson A P, Scharff O, Foder B, Cullen P J, Drobak B Y., Bjerrum, P J, Christensen S B, and Hanley M R. Thapsigargin, a novel molecular probe for studying intracellular calcium release and storage. Agents Actions 27: 17–23, 1989.
16. Toyoshima C, Nakasako M, Nomura H, and Ogawa H. Crystal structure of the calcium pump of sarcoplasmic reticulum at 2.6 A resolution. Nature 405: 647–655, 2000.
17. Van Breemen C and Saida Ys. Cellular mechanisms regulating $[Ca^{2+}]_i$ in smooth muscle. Annu Rev Physiol 5 1: 315–329, 1989.
18. Wuytack F, Raeymaekers L, Verbist J, De Smedt H, and Casteels R. Evidence for the presence in smooth muscle of two types of $Ca^{2+}$-transport ATPase. Biochem J 224: 445–451,1984.

We claim:

1. An isolated caloxin that can inhibit a plasma membrane $Ca^{2+}$-pump, selected from the group consisting of VSNSNWPSEPSSGGG (SEQ ID NO: 1), DSHINEPSRRRGGGK (SEQ ID NO: 2), and VSNSNWPSEPSS (SEQ ID NO: 6).

2. A method for isolating a caloxin comprising screening a random peptide phage display library with a peptide fragment from a PMCA protein and isolating peptides that bind to the PMCA peptide fragment.

3. An isolated caloxin prepared according to the method of claim 2.

* * * * *

SEQUENCE LISTING

```
<160> NUMBER OF SEQ ID NOS: 8

<210> SEQ ID NO 1
<211> LENGTH: 15
<212> TYPE: PRT
<213> ORGANISM: Homo sapiens

<400> SEQUENCE: 1

Val Ser Asn Ser Asn Trp Pro Ser Phe Pro Ser Ser Gly Gly Gly
1               5                   10                  15

<210> SEQ ID NO 2
<211> LENGTH: 16
<212> TYPE: PRT
<213> ORGANISM: Homo sapiens

<400> SEQUENCE: 2

Asp Ser His Ile Asn Asn Glu Pro Ser Arg Arg Arg Gly Gly Gly Lys
1               5                   10                  15
```

```
<210> SEQ ID NO 3
<211> LENGTH: 22
<212> TYPE: PRT
<213> ORGANISM: Artificial Sequence
<220> FEATURE:
<223> OTHER INFORMATION: Synthetic peptides

<400> SEQUENCE: 3

Trp Val Gln Lys Arg Pro Trp Leu Ala Glu Ser Thr Pro Ile Tyr Ile
1               5                   10                  15

Gln Tyr Phe Val Lys Cys
            20

<210> SEQ ID NO 4
<211> LENGTH: 10
<212> TYPE: PRT
<213> ORGANISM: Artificial Sequence
<220> FEATURE:
<223> OTHER INFORMATION: Synthetic peptides

<400> SEQUENCE: 4

Lys Ile Thr Gln Gly Ser Pro Leu Lys Ala
1               5                   10

<210> SEQ ID NO 5
<211> LENGTH: 15
<212> TYPE: PRT
<213> ORGANISM: Homo sapiens

<400> SEQUENCE: 5

Ser Trp Ser Ser Phe Pro Gly Ser Gly Gly Val Ser Asn Pro Asn
1               5                   10                  15

<210> SEQ ID NO 6
<211> LENGTH: 12
<212> TYPE: PRT
<213> ORGANISM: Homo sapiens

<400> SEQUENCE: 6

Val Ser Asn Ser Asn Trp Pro Ser Phe Pro Ser Ser
1               5                   10

<210> SEQ ID NO 7
<211> LENGTH: 11
<212> TYPE: PRT
<213> ORGANISM: Homo sapiens

<400> SEQUENCE: 7

Ser Trp Pro Ala Phe Pro Asn Ser Gly Glu Gly
1               5                   10

<210> SEQ ID NO 8
<211> LENGTH: 11
<212> TYPE: PRT
<213> ORGANISM: Homo sapiens

<400> SEQUENCE: 8

Asn Gln Gly Asn Trp Pro Asn Tyr Pro Ser Ser
1               5                   10
```